United States Patent [19]

VandenBerg

[11] Patent Number: Plant 6,586

[45] Date of Patent: Feb. 7, 1989

[54] CHRYSANTHEMUM PLANT NAMED LUCIDO

[75] Inventor: Cornelis P. VandenBerg, Salinas, Calif.

[73] Assignee: Yoder Brothers, Inc., Barberton, Ohio

[21] Appl. No.: 49,951

[22] Filed: May 15, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Lucido particularly characterized by its flat capitulum form; daisy capitulum type; red ray floret color; good color retention under high light conditions; diameter across face of capitulum of up to 7.5 cm at maturity when grown as a pinched spray pot mum; uniform eight week photoperiodic flowering response to short days; medium plant height when grown as a pinched pot mum; recommended as spray pot mum for all pot sizes; and spreading and prolific branching pattern.

3 Drawing Sheets

The present invention comprises a new and distinct cultivar of Chrysanthemum, botanically known as *Chrysanthemum morifolium*, Ramat., and referred to by the cultivar name Lucido.

Lucido, identified as 82263006, was originated from a cross made by Cornelius P. VandenBerg in a controlled breeding program in Salinas, Calif., in 1982.

The female parent of Lucido was an unnamed seedling, identified as 79Q55042. The male parent of Lucido was an unnamed seedling, identified as 79Q08005.

Lucido was discovered and selected as one flowering plant within the progeny of the stated cross by Cornelis P. VandenBerg in November of 1982, in a controlled environment in Salinas, Calif.

The first act of asexual reproduction of Lucido was accomplished when vegetative cuttings were taken from the initial selection in February of 1983 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Lucido are firmly fixed and are retained through successive generations of asexual reproduction.

Lucido has not been observed under all possible environmental conditions. The phenotype may vary significantly with variations in environment such as temperature, light intensity and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Lucido, which, in combination, distinguish this Chrysanthemum as a new and distinct cultivar:

1. Flat capitulum form.
2. Daisy capitulum type.
3. Red ray floret color.
4. Good color retention under high light conditions.
5. Diameter across face of capitulum up to 7.5 cm at maturity, when grown as a pinched spray pot mum.

6. Uniform eight week photoperiodic flowering response to short days.
7. Medium plant height requiring 0 to 7 long days after pinch prior to short days and 1 application of 2500 ppm B-9 SP to attain a flowered plant height of 25 to 35 cm for year-round flowerings when grown as a pinched pot mum.
8. Recommended as spray pot mum for all pot sizes.
9. Branching pattern is spreading and prolific.

The accompanying photographic drawings show typical inflorescence and leaf characteristics of Lucido, with the colors being as nearly true as possible with illustrations of this type.

Sheet 1 is a color photograph of Lucido grown as a pinched spray pot mum.

Sheet 2 is a black and white photograph of three views of the inflorescence of Lucido.

Sheet 3 is a black and white photograph showing the upper and under sides of the leaves of Lucido at three stages of development (mature, intermediate and immature).

Of the commercial cultivars known to the inventor, the most similar in comparison to Lucido is Alert, disclosed in U.S. Plant Pat. No. 5,365. Reference is made to attached Chart A, which compares certain characteristics of Lucido to the same characteristics of Alert.

Similar traits are capitulum form and type, plant height and flowering response. Ray floret color of Lucido is dark red, of Alert scarlet bronze. Lucido has a more spreading branching pattern and has a larger diameter of capitulum compared to Alert. Lucido develops pollen as the flowers mature, Alert develops no pollen.

In the following description color references are made to The Royal Horticultural Society Colour Chart. The exact colors for corolla of ray florets and disc florets are not represented in the R.H.S. Colour Chart, and the color values given are those closest to the actual color of Lucido. The color values were determined on plant material grown as a pinched spray pot mum in Salinas, Calif. on Dec. 16, 1986.

Classification:

*Botanical.—Chrysanthemum morifolium*, Ramat., cv Lucido

*Commercial.*—Daisy spray pot mum.

INFLORESCENCE

A. Capitulum:
- *Form.*—Flat.
- *Type.*—Daisy.
- *Diameter across face.*—Up to 7.5 cm at maturity.

B. Corolla of ray florets:
- *Color (general tonality from a distance of three meters).*—Red.
- *Color (upper surface).*—46A to 53A.
- *Color (under surface).*—179C, heavily streaked with 179A to 179B.
- *Shape.*—Flat; oblong.

C. Corolla of disc florets:
- *Color (mature).*—9B.
- *Color (immature).*—154A to 154B.

D. Reproductive organs:
- *Androecium.*—Present in disc florets only; abundant pollen.
- *Gynoecium.*—Present in both ray and disc florets.

PLANT

A. General appearance:
- *Height.*—Medium: 25 to 35 cm as a pinched spray pot mum with 0 to 7 long days after pinch prior to short days and 1 application of 2500 ppm B-9 SP. Branching pattern: Spreading and prolific.

B. Foliage:
- *Color (upper surface).*—147A.
- *Color (under surface).*—147B.
- *Shape.*—Deeply lobed and serrated.

CHART A

Comparison of LUCIDO and ALERT

| CULTIVAR | RAY FLORET COLOR | CAPITULUM FORM & TYPE | BRANCHING PATTERN |
|---|---|---|---|
| LUCIDO | RED | FLAT DAISY | SPREADING and PROLIFIC |
| ALERT | SCARLET BRONZE | FLAT DAISY | SEMI UPRIGHT |

| CULTIVAR | DIAMETER ACROSS FACE OF CAPITULUM | PLANT HEIGHT | FLOWERING RESPONSE PERIOD | POLLEN |
|---|---|---|---|---|
| LUCIDO | Up to 7.5 cm. | MEDIUM | 8 WEEK | ABUNDANT |
| ALERT | 55 to 65 mm. | MEDIUM | 8 WEEK | NONE |

COMPARISONS MADE OF PLANTS GROWN AS PINCHED SPRAY POT MUMS IN SALINAS, CALIFORNIA AND LEAMINGTON, CANADA

I claim:

1. A new and distinct Chrysanthemum plant named Lucido, as described and illustrated, and particularly characterized as to uniqueness by the combined characteristics of flat capitulum form; daisy capitulum type; red ray floret color; good color retention under high light conditions; diameter across face of capitulum of up to 7.5 cm at maturity when grown as a pinched spray pot mum; uniform eight week photoperiodic flowering response to short days; medium plant height when grown as a pinched pot mum; recommended as spray pot mum for all pot sizes; and spreading and prolific branching pattern.

* * * * *

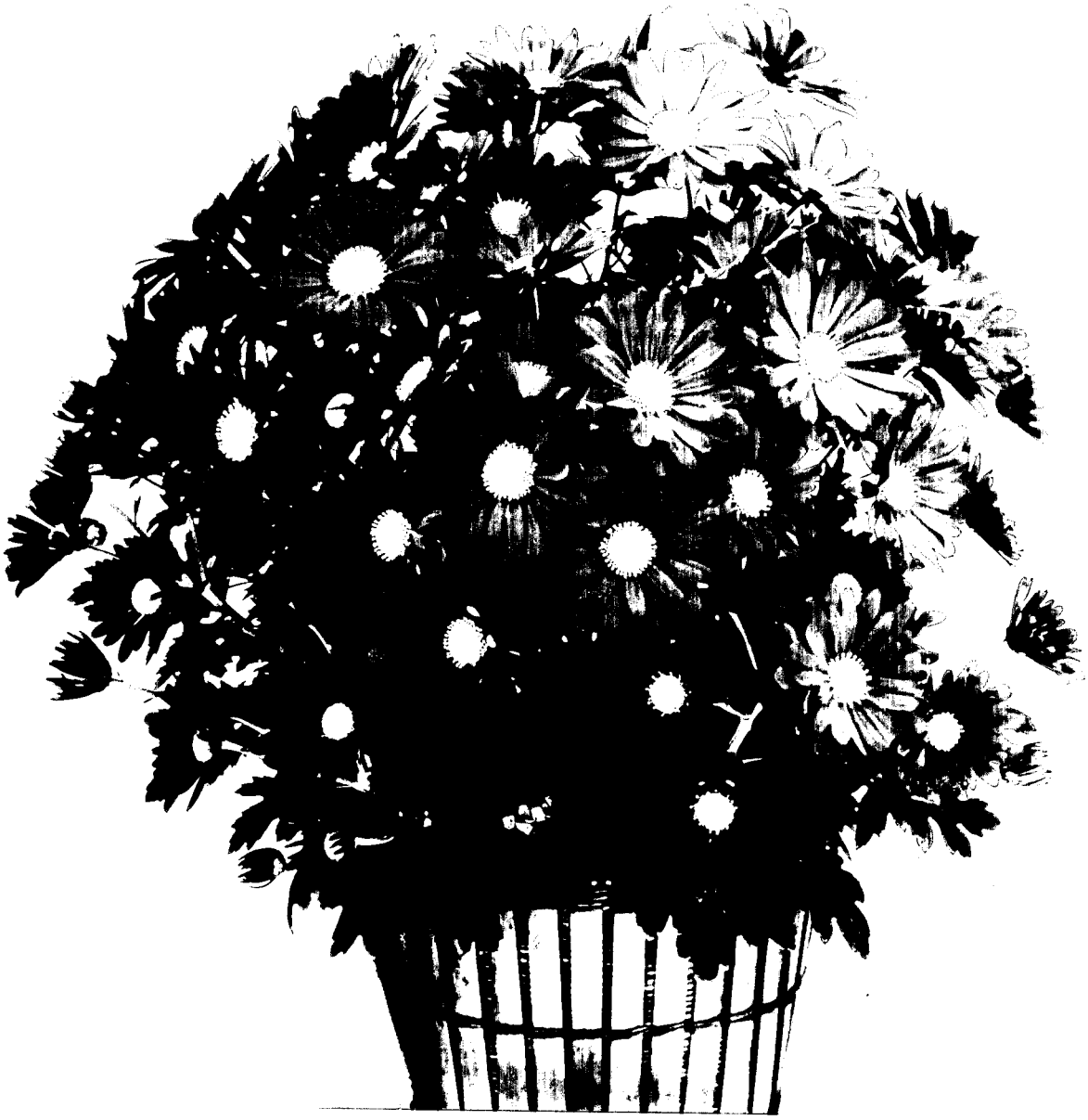

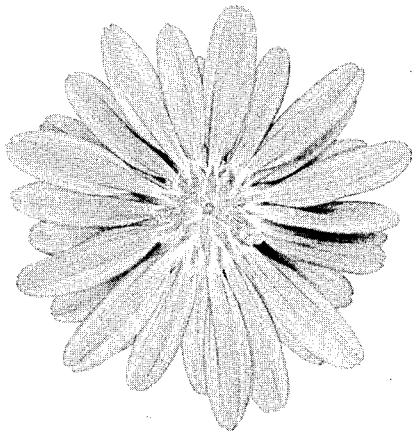
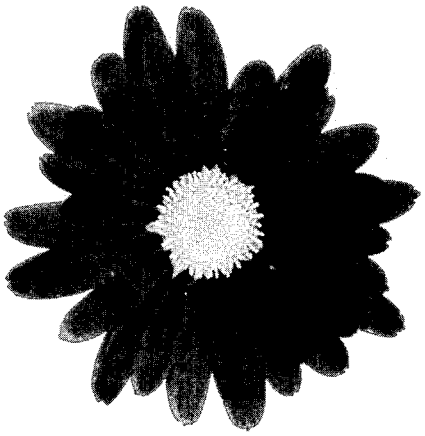
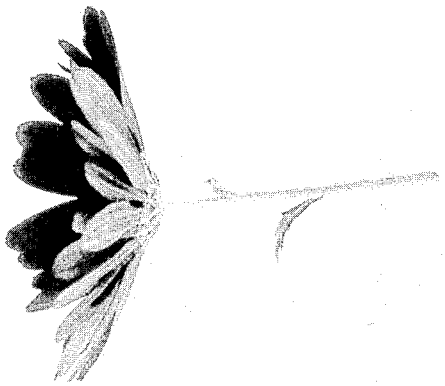

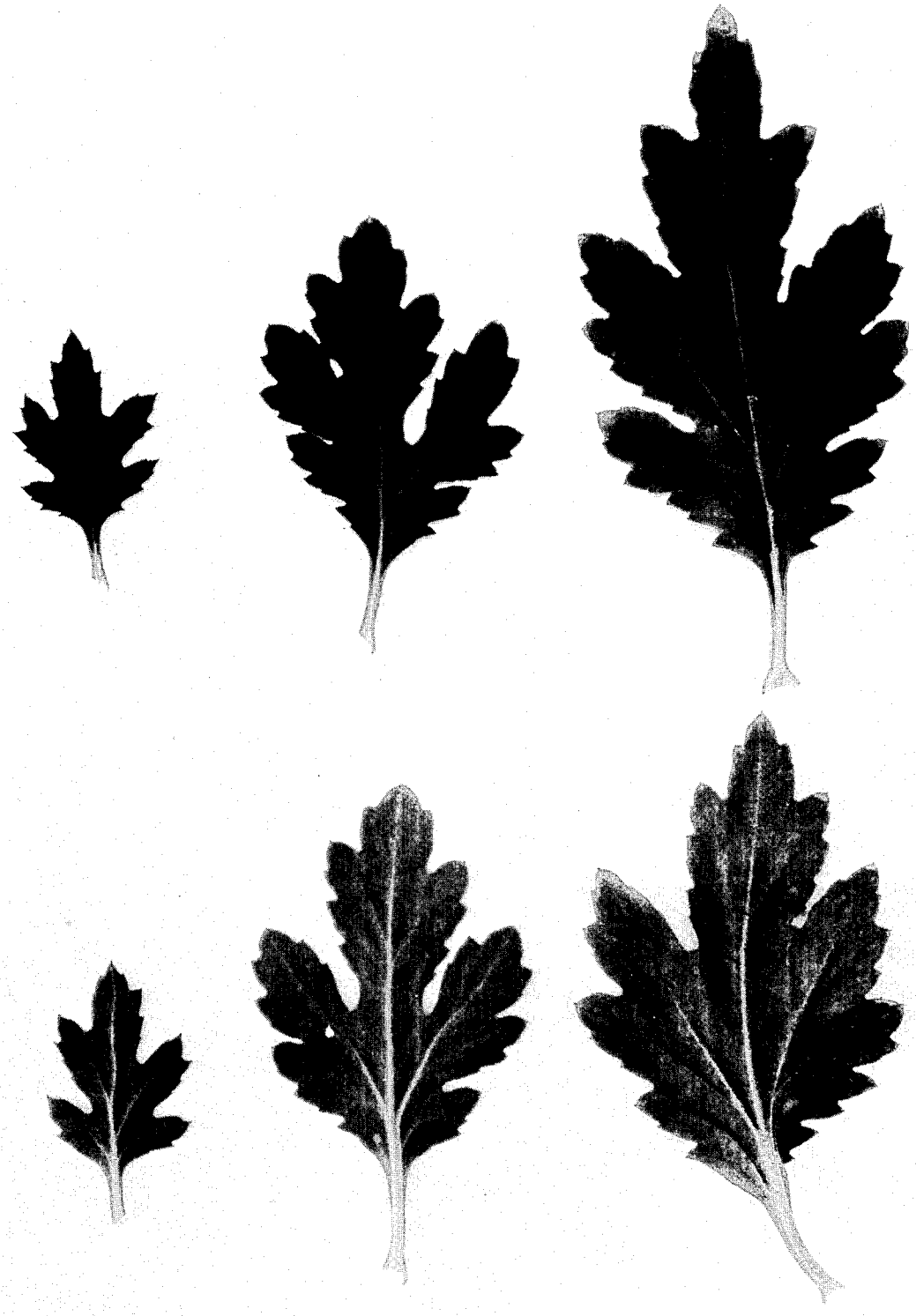

UNITED STATES PATENT AND TRADEMARK OFFICE

CERTIFICATE OF CORRECTION

PATENT NO. : PP 6,586

DATED : February 7, 1989

INVENTOR(S) : Cornelis P. VandenBerg

It is certified that error appears in the above—identified patent and that said Letters Patent is hereby corrected as shown below:

Column 1, Line 6, "Cornelius" should be "Cornelis".

Column 3, Line 30, after "SP." a paragraph should appear. In the new line which would then follow, "Branching pattern" should appear in italics.

Signed and Sealed this

Third Day of July, 1990

*Attest:*

HARRY F. MANBECK, JR.

*Attesting Officer*

*Commissioner of Patents and Trademarks*